(12) United States Patent
Kuan

(10) Patent No.: US 7,355,173 B2
(45) Date of Patent: Apr. 8, 2008

(54) DELINEATION OF WAFERS

(75) Inventor: Hing Poh Kuan, Singapore (SG)

(73) Assignee: Systems On Silicon Manufacturing Co., Pte. Ltd., Singapore (SG)

( * ) Notice: Subject to any disclaimer, the term of this patent is extended or adjusted under 35 U.S.C. 154(b) by 19 days.

(21) Appl. No.: 11/030,500

(22) Filed: Jan. 6, 2005

(65) Prior Publication Data

US 2006/0145074 A1    Jul. 6, 2006

(51) Int. Cl.
*G01N 23/00* (2006.01)
(52) U.S. Cl. .................... 250/307; 438/692; 438/708; 451/41
(58) Field of Classification Search ............... 250/307; 438/692, 708; 451/41
See application file for complete search history.

(56) References Cited

U.S. PATENT DOCUMENTS 5,851,925 A * 12/1998 Beh et al. ................. 438/708
2003/0171075 A1 * 9/2003 Nihonmatsu et al. ......... 451/41

* cited by examiner

*Primary Examiner*—David Vanore
(74) *Attorney, Agent, or Firm*—Harness, Dickey & Pierce, P.L.C.

(57) ABSTRACT

A method of junction delineation of non-epitaxial wafers comprises the steps of preparing a sample of the wafer, staining the sample using a mixture of between one and three parts hydrofluoric acid to fifty parts nitric acid to twenty parts water, and scanning the sample with a scanning electron microscope.

14 Claims, 4 Drawing Sheets

DELINEATION OF WAFERS

BACKGROUND OF THE INVENTION

1. Field of the Invention

The present invention relates to delineation of wafers and in particular to delineation of junctions within wafers.

2. Description of the Prior Art

Silicon wafer fabrication techniques are used in the fabrication of integrated circuits. Integrated circuits form the basis of microelectromechanical devices (MEMS), computer processors, computer memory and many other devices. After the integrated circuits are formed they are tested to ensure that the fabrication process has produced operative devices.

Fault testing of integrated circuits involves probing the fabricated devices at different points and applying an electrical current between the probe points. Electrical characteristics between the probe points are then measured and provide an indication of whether or not the device is operating correctly.

There may be many causes of why a device does not operate correctly when probed. These could be a failure in the probing equipment or a failure in the device itself. If the failure is in the device and recurs frequently in devices made by the same process this could indicate that the manufacturing process needs to be adjusted to correct or prevent the failure.

One cause of failure in device can occur in the doping profile of a silicon wafer where one type of doping extends further through the wafer than required. This can lead to current leakage which can cause failures in devices. For example current leakage can occur in a p-n-p junction of a transistor where the two p layers are not sufficiently separated by the n layer. When a current is applied to the transistor it may leak through the n layer causing the transistor to malfunction.

If a fault in a device occurs in the doping profile of a silicon wafer this cannot be easily detected using microscopy as the different doping profiles of the silicon cannot be visually distinguished.

One current method used to view silicon implantation defects is to cut a sample from the device. The sample is then mounted and polished. The cross-sectional surface must have low roughness, no surface damage and high cleanliness. The sample receives a final polish using colloidal silica solution to provide the required sample quality. To improve the reproducibility of the results the surface can be coated with native oxide to eliminate any non-uniform charge distribution that remains after the polishing stages. The samples are then scanned with a SCM (scanning capacitance microscope). This system requires a skilled operator to operate the SCM to detect junction faults.

BRIEF SUMMARY OF THE INVENTION

Accordingly to the present invention there is provided a method of junction delineation of non-epitaxial wafers comprising the steps of preparing a sample of the wafer, staining the sample using a mixture of one to three parts hydrofluoric acid to between forty and sixty parts nitric acid to twenty parts water, and scanning the sample with a scanning electron microscope.

In one embodiment the sample of the wafer is prepared by top down de-processing of the sample.

If the sample if prepared by top down de-processing of the sample preferably the step of staining the wafer comprises staining the wafer for about three to five seconds.

In an alternative embodiment the sample of the wafer is prepared by cleaving a cross section from the wafer.

If the sample is prepared by cleaving a portion of the wafer preferably the step of staining the wafer comprises staining the wafer for about three to five seconds.

In another alternative embedment the sample of the wafer is prepared by polishing a cross section of the wafer.

If the sample of the wafer is prepared by polishing the cross section of the wafer preferably the step of staining the wafer comprises staining the wafer for about twelve to fifteen seconds.

Preferably the method of junction delineation includes an initial step of detecting a fault in a wafer during testing.

In broad terms in another embodiment the invention comprises a method of junction delineation of epitaxial wafers comprising the steps of preparing a sample of the wafer, staining the sample using a mixture of one to three parts hydrofluoric acid to between ten and thirty parts nitric acid to twenty parts acetic acid, and scanning the sample with a scanning electron microscope.

In one embodiment the sample of the wafer is prepared by cleaving a cross section from the wafer.

If the sample is prepared by cleaving a portion of the wafer preferably the step of staining the wafer comprises staining the wafer for about five to eight seconds.

In another alternative embedment the sample of the wafer is prepared by polishing a cross section of the wafer.

If the sample of the wafer is prepared by polishing the cross section of the wafer preferably the step of staining the wafer comprises staining the wafer for about five to eight seconds.

Preferably the method of junction delineation includes an initial step of detecting a fault in a wafer during testing.

BRIEF DESCRIPTION OF THE SEVERAL VIEWS OF THE DRAWINGS

The invention will be further described by way of example only and without intending to be limiting with reference to the following drawings, wherein.

DETAILED DESCRIPTION OF THE INVENTION

Figure 1:
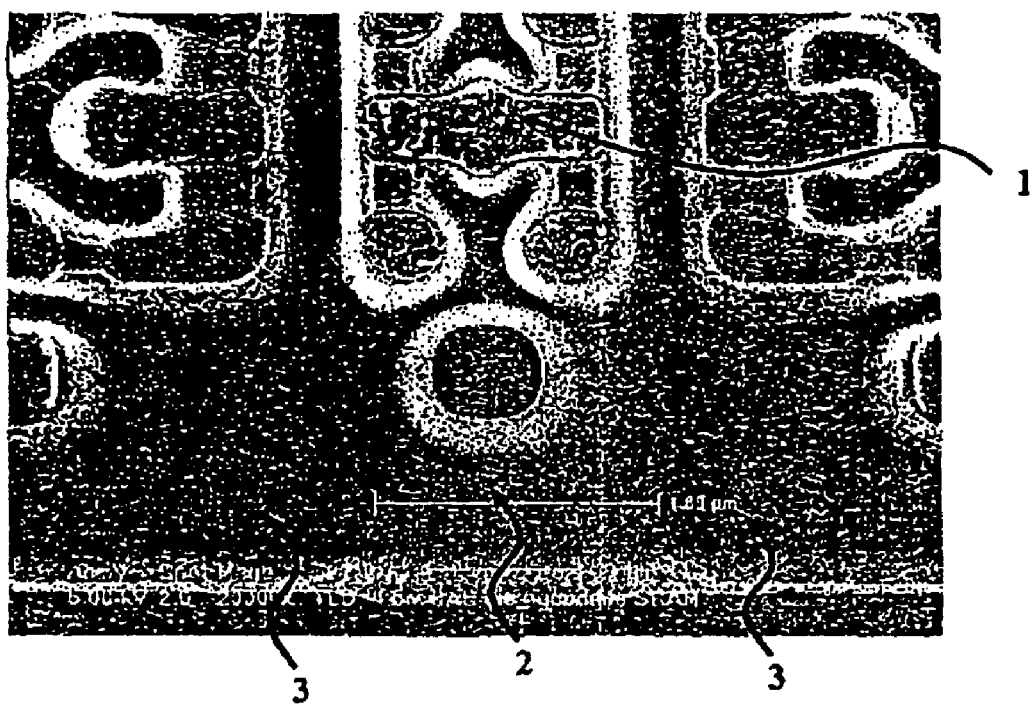
FIG. 1 is a top view of a first wafer sample of a bad die.

FIG. 1 shows a top view of a first wafer sample of a bad die. This sample has been subjected to top down de-processing. Top down de-processing of a device comprises removing layers of the device using etching or other suitable techniques. Top down de-processing can be used when it is uncertain where a fault occurs in a device. This process allows the device to be viewed as each layer is removed and irregularities in each layer of the device can be noted.

After de-processing the device in FIG. 1 to the silicon wafer layer the device is stained with a mixture of hydrofluoric acid, nitric acid and water. The proportions of the mixture are one part hydrofluoric acid to fifty parts nitric acid to twenty parts water by volume. The hydrofluoric acid is in a solution of 49% hydrofluoric acid and the nitric acid is in a solution of 69% nitric acid. The sample is subjected to the stain for about five seconds and in preferred embodiments for between three and five seconds.

After staining the sample is viewed using a scanning electron microscope. FIG. 1 shows the sample as viewed by the scanning electron microscope. As can be seen in FIG. 1 there is a central p-doped area 1 that is surrounded by an n-well 2. A further p-doped area 3 surrounds the n-well 2. In this figure the n-well is 1.89 microns wide and is close to one edge of the central p-doped area 1. This is where leakage across the wafer may occur. As can been seen in this Figure the staining makes the boundary between the p-doped 1 area and the n-well 2 clearly visible. This allows the different doping in the silicon wafer to be differentiated using the scanning electron microscope.

Figure 3:
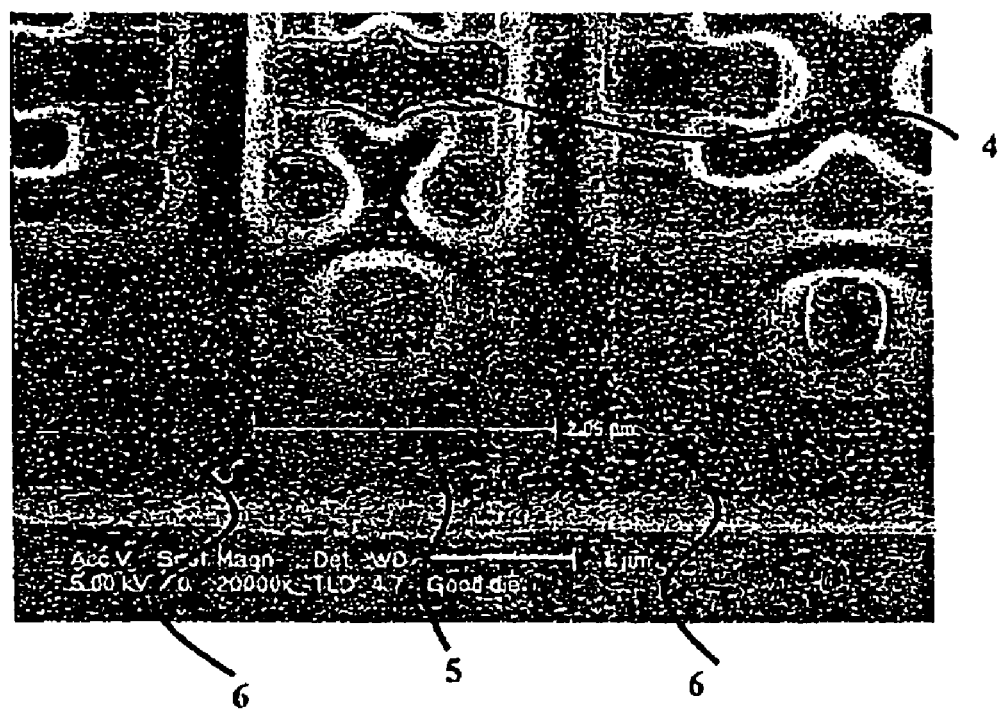
FIG. 3 is a top view of a third wafer sample of a good die.

FIG. 3 shows a top view of a third wafer sample of a good die. This sample has been subjected to top down de-processing. After de-processing the device in FIG. 3 to the silicon wafer layer the device is stained with a mixture of hydrofluoric acid, nitric acid and water. The proportions of the mixture are one part hydrofluoric acid to fifty parts nitric acid to twenty parts water by volume. The sample is subjected to the stain for about five seconds and in preferred embodiments for between three and five seconds.

After staining the sample is viewed using a scanning electron microscope. FIG. 3 shows the sample as viewed by the scanning electron microscope. As can be seen in FIG. 3 there is a central p-doped area 4 that is surrounded by an n-well 5. A further p-doped area 6 surrounds the n-well 5. In this figure the n-well is 2.05 microns wide and is spaced evenly about the central p-doped area 4.

Contrasting FIGS. 1 and 3 shows the difference between a bad die where the n-well is insufficient around one portion of the p-doped silicon and a good die where the n-well is sufficient and no current leakage will occur. The comparison of the good die to the bad die allows the manufacturing process to be altered to overcome the fault.

Figure 2:
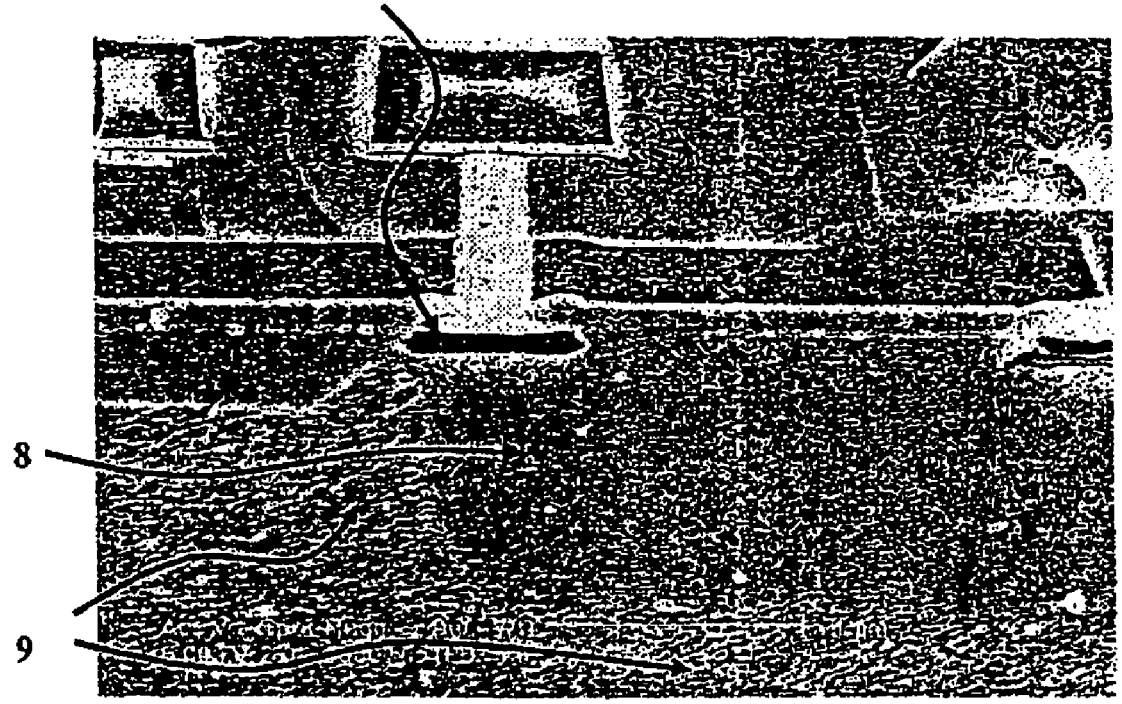
FIG. 2 is a side view of a second wafer sample of a bad die.

FIG. 2 shows a side view of a second wafer sample of a bad die. This sample has been subjected to cleaving. Cleaving a sample comprises cutting a sample from a device using any suitable technique. This process provides a cross section of the die.

After cleaving a sample from the device in FIG. 2 the sample is stained with a mixture of hydrofluoric acid, nitric acid and water. The proportions of the mixture are one part hydrofluoric acid to fifty parts nitric acid to twenty parts water by volume. The hydrofluoric acid is in a solution of 49% hydrofluoric acid and the nitric acid is in a solution of 69% nitric acid. The sample is subjected to the stain for about five seconds and in preferred embodiments for between three and five seconds.

After staining the sample is viewed using a scanning electron microscope. FIG. 2 shows the sample as viewed by the scanning electron microscope. As can be seen in FIG. 2 there is a p-doped area 7 that is above an n-well 8. A further p-doped area 9 is situated to the left and underneath the n-well. In this figure the p-doped area to the left of the n-well extends close to p-doped area 7 with a very minimal amount of the n-well between the two p-doped areas. This is where leakage across the wafer may occur.

Figure 4:
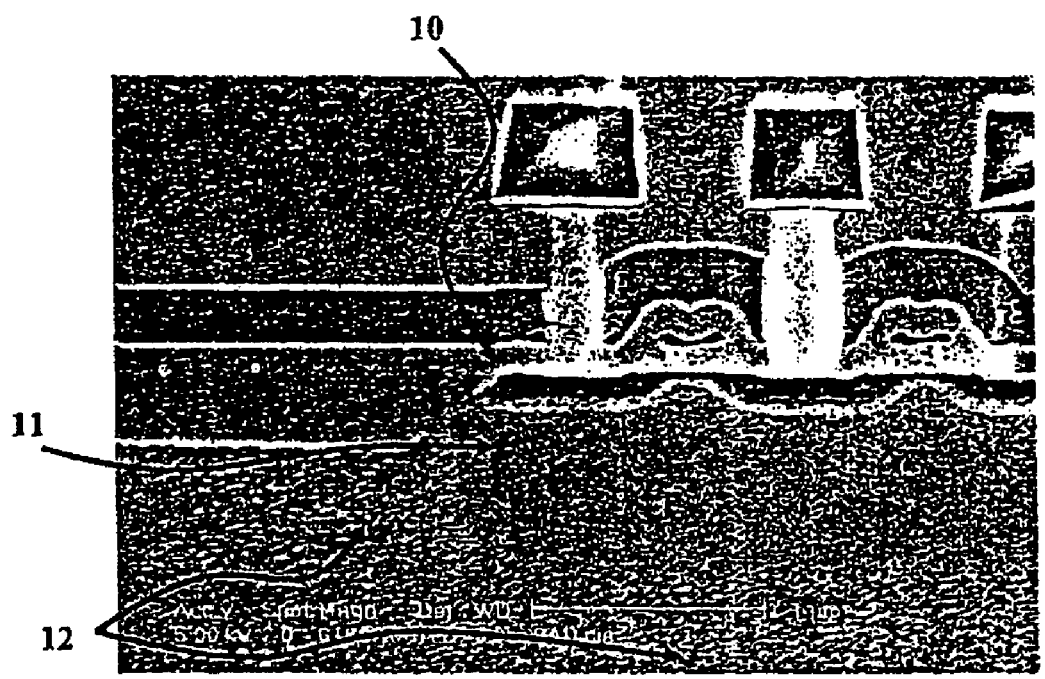
FIG. 4 is a side view of a fourth wafer sample of a good die.

FIG. 4 shows a side view of a fourth wafer sample of a good die. This sample has been subjected to cleaving. Cleaving a sample comprises cutting a sample from a device using any suitable technique. This process provides a cross section of the die.

After cleaving a sample from the device in FIG. 4 the sample is stained with a mixture of hydrofluoric acid, nitric acid and water. The proportions of the mixture are one part hydrofluoric acid to fifty parts nitric acid to twenty parts water by volume. The hydrofluoric acid is in a solution of 49% hydrofluoric acid and the nitric acid is in a solution of 69% nitric acid. The sample is subjected to the stain for about five seconds and in preferred embodiments for between three and five seconds.

After staining the sample is viewed using a scanning electron microscope. FIG. 4 shows the sample as viewed by the scanning electron microscope. As can be seen in FIG. 4 there is a p-doped area 10 that is above an n-well 11. A further p-doped area 12 is situated to the left and underneath the n-well. In this figure the p-doped area to the left of the n-well extends close to p-doped area 10 with a sufficient amount of the n-well between the two p-doped areas and no leakage across the wafer occurs.

The staining allows the differently doped areas to silicon to be easily viewed using the scanning electron microscope and allows the problem areas on a die to be easily identified as shown in FIGS. 2 and 4.

The invention has been successful in all examples to date and does not require a skilled operator to operate the SEM.

FIGS. 1 to 4 show the use of the invention in detecting Iddq leakage across transistors. However the invention is not limited to the detection of this type of fault and can be used to detect many faults that are related to doping of silicon wafers.

Figure 5:
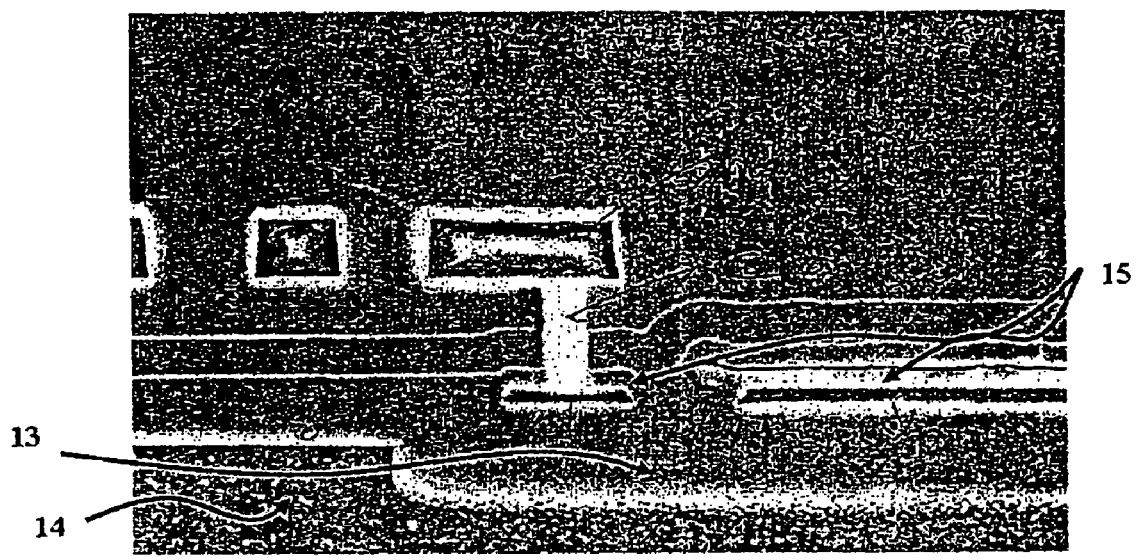
FIG. 5 is a side view of a fifth wafer sample.

FIG. 5 shows a cleaved sample after SEM. This sample is from a non-epitaxial wafer and after cleaving has been stained for about three seconds. The staining process works as a two-stage mechanism by first oxidising the silicon and the removing the silicon dioxide. In chemical terms this process can be described as

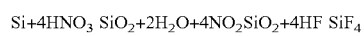

$$Si + 4HNO_3 \rightarrow SiO_2 + 2H_2O + 4NO_2 SiO_2 + 4HF \rightarrow SiF_4$$

As can be seen in FIG. 5 the staining has illuminated the boundaries between the p-substrate 13, the n-well 14, and the p+ substrate 15.

Figure 6:
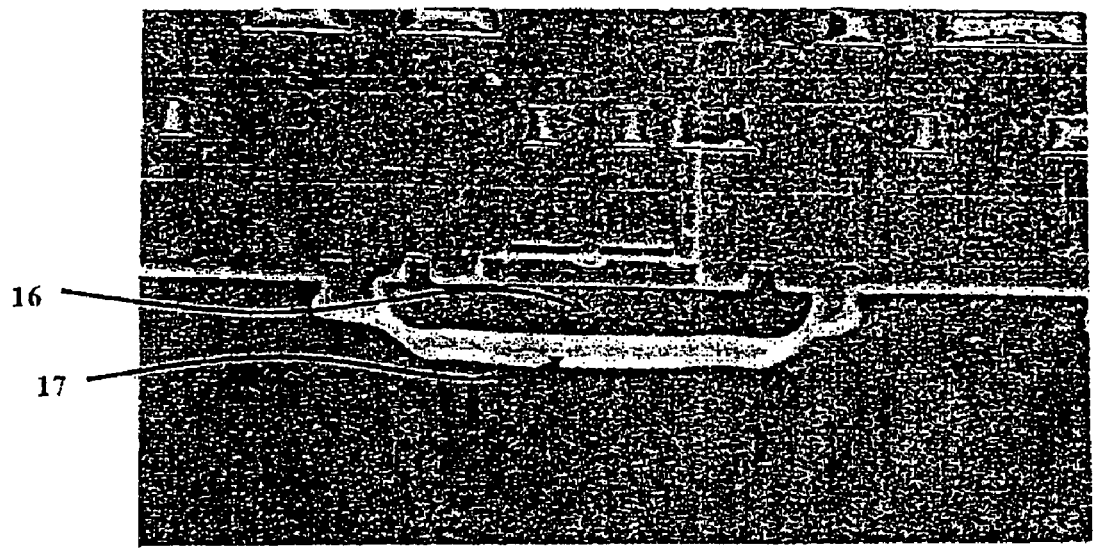
FIG. 6 is a side view of a sixth wafer sample.

FIG. 6 shows a cleaved sample after SEM. This sample is from an epitaxial wafer and after cleaving has been stained for about eight seconds to stain out a buried n-well. The staining process works as a two-stage mechanism by first oxidising the silicon and the removing the silicon dioxide. In chemical terms this process can be described as

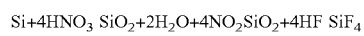

$$Si + 4HNO_3 \rightarrow SiO_2 + 2H_2O + 4NO_2 SiO_2 + 4HF \rightarrow SiF_4$$

As can be seen in FIG. 6 the staining has illuminated the boundaries between the p-well 16 and the buried n-well 17.

As can be seen by the staining times given in these examples it is easier to stain out a non-epitaxial wafer than an epitaxial wafer. However either type of wafer can be stained using the method of the invention. It should be noted that the chemical formulation used to stain the wafers depends on whether the wafer being stained is an epitaxial or a non-epitaxial wafer. If the wafer is a non-epitaxial wafer the preferred staining formulation is one part hydrofluoric acid (HF(49%)) to fifty parts nitric acid ($HNO_3$(69%)) to twenty parts water ($H_2O$). If the wafer is a non-epitaxial wafer the formulation may be one part hydrofluoric acid to between forty and sixty parts nitric acid to twenty parts water by volume. If the wafer is an epitaxial wafer the preferred staining formulation is one part hydrofluoric acid (HF (49%)) to twenty parts nitric acid (HNO$_3$) to twenty parts acetic acid (CH$_3$COOH). If the wafer is an epitaxial wafer the staining formulation may be one part hydrofluoric acid to between ten and thirty parts nitric acid to twenty parts acetic acid by volume.

The variation in the ratio of hydrofluoric acid to nitric acid to water for junction delineation of non-epitaxial wafers is (1-3) parts HF: (40 to 60) parts HNO$_3$: 20 parts H$_2$O. The variation in the ratio of hydrofluoric acid to nitric acid to acetic acid for junction delineation of epitaxial wafers is (1 to 3) parts HF: (10 to 30) parts HNO$_3$: 20 parts CH$_3$COOH.

The invention makes use of the different etching rates of silicon substrates with different dopant concentrations and type to provide junction delineation. For non-epitaxial wafers the etch rates between different dopant regions (for example p-type and n-type regions) is quite different. In this case water can be used as a diluent. For epitaxial wafers the etch rate is comparable between different dopant regions. This makes the task of delineating the regions difficult. Using acetic acid as a diluent the etch rate at the different doping regions on the wafer can be controlled so as to provide an adequate contrast between the p-type and n-type regions.

Figure 7:
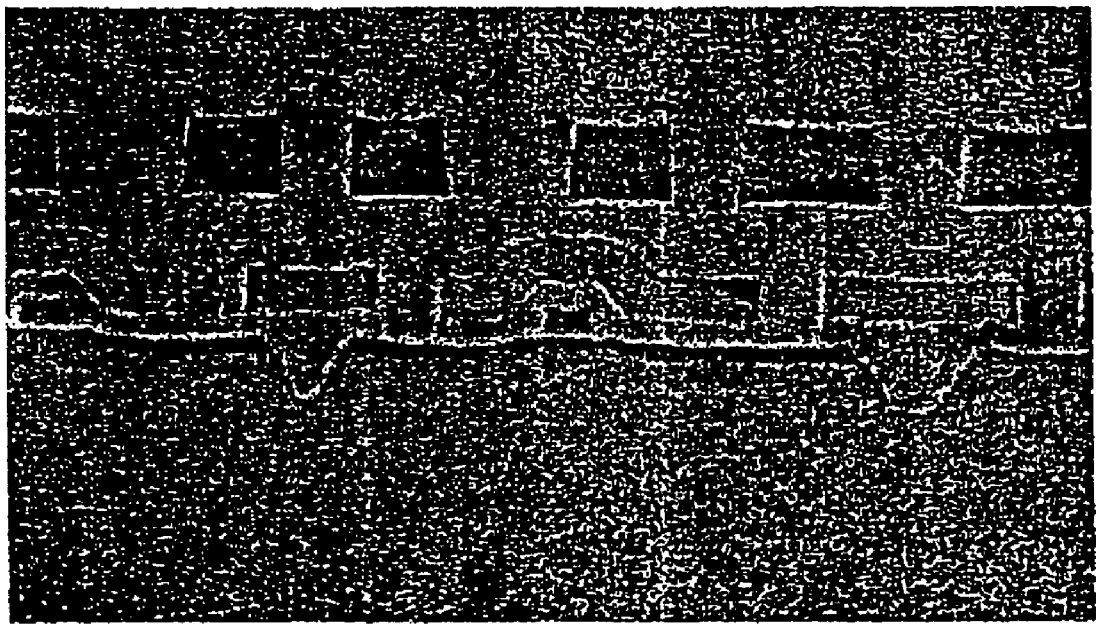
FIG. 7 is a side view of a seventh wafer sample.

FIG. 7 shows a polished sample after SEM. This sample is from a non-epitaxial wafer and after fine cloth polishing and staining for about twelve seconds. The stain times for samples that have been polished are preferably between twelve and fifteen seconds. The formulation used to stain the sample is one part hydrofluoric acid to fifty parts nitric acid to twenty parts water. The areas within the silicon wafer that have been doped with different dopants are clearly visibly in the SEM image of FIG. 7.

Figure 8:
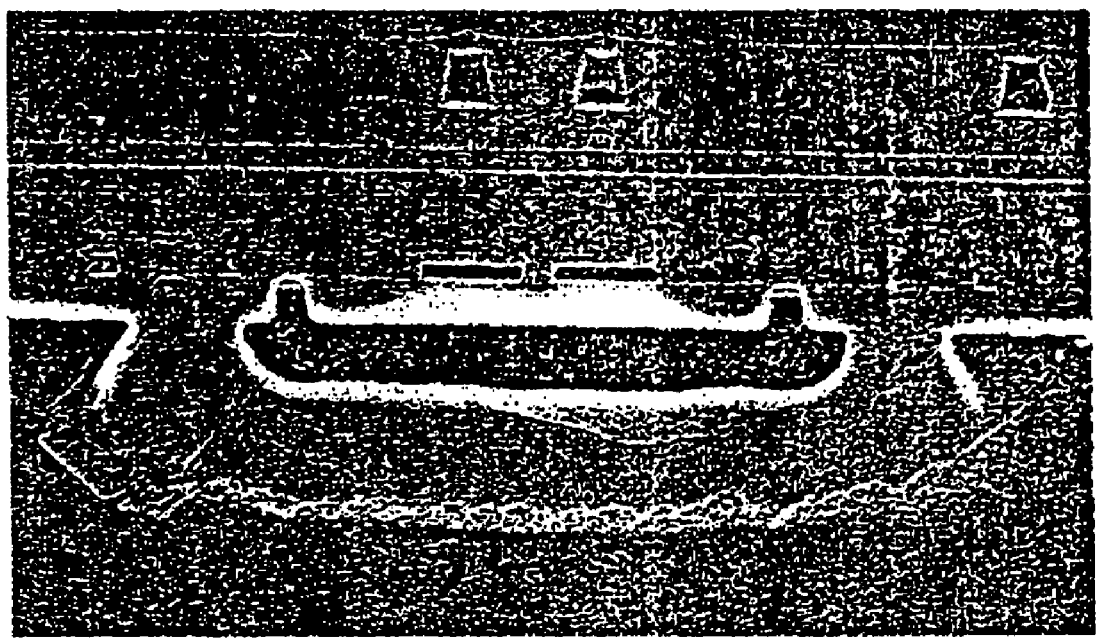
FIG. 8 is a side view of an eighth wafer sample.

FIG. 8 shows a polished sample after SEM. This sample is from an epitaxial wafer and after fine cloth polishing and staining for about eight seconds. The stain times for samples that have been polished are preferably between five and eight seconds. The formulation used to stain the sample is one part hydrofluoric acid to twenty parts nitric acid to twenty parts acetic acid. The areas within the silicon wafer that have been doped with different dopants are clearly visibly in the SEM image of FIG. 8. For example the p-well is distinctly stained in FIG. 8.

It has been found that when polishing samples prior to staining the samples a cloth polisher for fine polishing helps to stain out p-n junctions more clearly.

The advantages of the process of the invention include that many different sample preparations can be used and adequate junction delineation is produced. Different sample preparations include top down de-processing of the die, cleaving a cross section from a die, and polishing a cross section of the die. Following any of these processes on an epitaxial or non-epitaxial wafer the wafer is stained and then scanned with a scanning electron microscope. This process is quick and simple.

Another advantage of the current method is that is can be performed at room temperature with equal or greater sensitivity and reproducibility when compared to scanning capacitive microscopy methods.

The foregoing describes the invention including preferred forms thereof. Alterations and modifications as will be obvious to those skilled in the art are intended to be incorporated in the scope hereof as defined by the accompanying claims.

I claim:

1. A method of junction delineation of non-epitaxial wafers comprising the steps of preparing a sample of the wafer,
staining the sample using a mixture of between one and three parts hydrofluoric acid to between forty and sixty parts nitric acid to twenty parts water by volume, and
scanning the sample with a scanning electron microscope.

2. A method of junction delineation of non-epitaxial wafers as claimed in claim 1 wherein the sample of the wafer is prepared by top down de-processing of the sample.

3. A method of junction delineation of non-epitaxial wafers as claimed in claim 2 wherein the step of staining the wafer comprises staining the wafer for about three to five seconds.

4. A method of junction delineation of non-epitaxial wafers as claimed in claim 1 wherein the sample of the wafer is prepared by cleaving a cross section from the wafer.

5. A method of junction delineation of non-epitaxial wafers as claimed in claim 4 wherein the step of staining the wafer comprises staining the wafer for about three to five seconds.

6. A method of junction delineation of non-epitaxial wafers as claimed in claim 1 wherein the sample of the wafer is prepared by polishing a cross section of the wafer.

7. A method of junction delineation of non-epitaxial wafers as claimed in claim 6 wherein the step of staining the wafer comprises staining the wafer for about twelve to fifteen seconds.

8. A method of junction delineation of non-epitaxial wafers as claimed in claim 1 wherein the method of junction delineation includes an initial step of detecting a fault in a wafer during testing.

9. A method of junction delineation of epitaxial wafers comprising the steps of preparing a sample of the wafer,
staining the sample using a mixture of between one and three parts hydrofluoric acid to between ten and thirty parts nitric acid to twenty parts acetic acid by volume, and
scanning the sample with a scanning electron microscope.

10. A method of junction delineation of epitaxial wafers as claimed in claim 9 wherein the sample of the wafer is prepared by cleaving a cross section from the wafer.

11. A method of junction delineation of epitaxial wafers as claimed in claim 10 wherein the step of staining the wafer comprises staining the wafer for about five to eight seconds.

12. A method of junction delineation of epitaxial wafers as claimed in claim 9 wherein the sample of the wafer is prepared by polishing a cross section of the wafer.

13. A method of junction delineation of epitaxial wafers as claimed in claim 12 wherein the step of staining the wafer comprises staining the wafer for about five to eight seconds.

14. A method of junction delineation of epitaxial wafers as claimed in claim 9 wherein the method of junction delineation includes an initial step of detecting a fault in a wafer during testing.

* * * * *